(12) United States Patent
Hörner et al.

(10) Patent No.: US 9,822,197 B2
(45) Date of Patent: Nov. 21, 2017

(54) METHOD FOR PRODUCING SUPERABSORBERS BASED ON RENEWABLE RAW MATERIALS

(71) Applicant: BASF SE, Ludwigshafen (DE)

(72) Inventors: Klaus Dieter Hörner, Lampertheim (DE); Jürgen Schröder, Ludwigshafen (DE); Rüdiger Funk, Niedernhausen (DE); Renate Wüstefeld, Speyer (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/441,203

(22) PCT Filed: Nov. 18, 2013

(86) PCT No.: PCT/EP2013/074007
§ 371 (c)(1),
(2) Date: May 7, 2015

(87) PCT Pub. No.: WO2014/079785
PCT Pub. Date: May 30, 2014

(65) Prior Publication Data
US 2015/0299347 A1   Oct. 22, 2015

Related U.S. Application Data

(60) Provisional application No. 61/729,645, filed on Nov. 26, 2012.

(30) Foreign Application Priority Data

Nov. 26, 2012   (EP) .................................... 12194209

(51) Int. Cl.
| | |
|---|---|
| C07C 51/16 | (2006.01) |
| C07C 51/245 | (2006.01) |
| C08L 31/00 | (2006.01) |
| C08L 33/00 | (2006.01) |
| C09D 5/02 | (2006.01) |
| C08F 2/00 | (2006.01) |
| C08F 120/06 | (2006.01) |
| A61L 15/60 | (2006.01) |
| C07C 51/215 | (2006.01) |
| C07C 51/25 | (2006.01) |
| C08F 220/06 | (2006.01) |
| C10G 3/00 | (2006.01) |
| C07C 1/20 | (2006.01) |
| C08J 3/24 | (2006.01) |

(52) U.S. Cl.
CPC ............ *C08F 120/06* (2013.01); *A61L 15/60* (2013.01); *C07C 1/20* (2013.01); *C07C 51/215* (2013.01); *C07C 51/252* (2013.01); *C08F 220/06* (2013.01); *C08J 3/245* (2013.01); *C10G 3/40* (2013.01); *C08J 2333/02* (2013.01); *C10G 2300/1014* (2013.01); *C10G 2400/20* (2013.01)

(58) Field of Classification Search
None
See application file for complete search history.

(56) References Cited

U.S. PATENT DOCUMENTS

| | | | |
|---|---|---|---|
| 2004/0015011 A1* | 1/2004 | Krokoszinski | C07C 45/33 562/521 |
| 2006/0004229 A1 | 1/2006 | Dieterle et al. | |
| 2009/0134357 A1 | 5/2009 | Bub et al. | |
| 2011/0224379 A1* | 9/2011 | Bruhns | A61L 15/60 525/327.3 |
| 2012/0157728 A1* | 6/2012 | Vermeiren | C11B 3/12 585/240 |

FOREIGN PATENT DOCUMENTS

| | | |
|---|---|---|
| DE | 1 033 6386 A1 | 3/2004 |
| EP | 2 290 034 A1 | 3/2011 |
| EP | 2 290 045 A1 | 3/2011 |
| EP | 2 395 029 A1 | 12/2011 |
| WO | WO-2006/092272 A2 | 9/2006 |

OTHER PUBLICATIONS

Buchholz, Fredric L., et al. *Modern Superabsorbent Polymer Technology*, "Commercial Processes for the Manufacture of Superabsorbent Polymers." New York: John Wiley & Sons, Inc., 1998, pp. 71-103.

International Search Report for international application No. PCT/EP2013/074007, dated Nov. 19, 2014.

* cited by examiner

*Primary Examiner* — Robert T Butcher
(74) *Attorney, Agent, or Firm* — Marshall, Gerstein & Borun LLP

(57) ABSTRACT

A process for producing water-absorbing polymer particles, comprising the steps of thermal cracking of bionaphtha in the presence of steam, removing propene and at least some of the propane, gas phase oxidation to give acrylic acid and polymerization to give water-absorbing polymer particles.

7 Claims, 3 Drawing Sheets

METHOD FOR PRODUCING SUPERABSORBERS BASED ON RENEWABLE RAW MATERIALS

CROSS-REFERENCE TO RELATED APPLICATIONS

Figure 1:
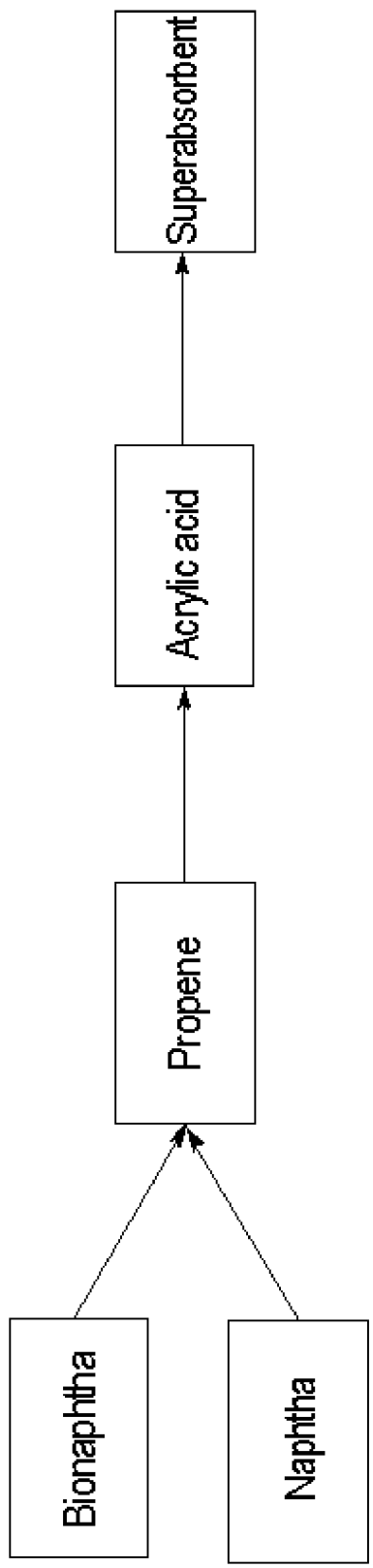

This is the U.S. National Stage of PCT/EP2013/074007, filed Nov. 18, 2013, which claims the benefit of EP Patent Application No. 12194209.8, filed Nov. 26, 2012, and U.S. Provisional Patent Application No. 61/729,645, filed Nov. 26, 2012, incorporated herein by reference in its entirety.

The present invention relates to a process for producing water-absorbing polymer particles, comprising the steps of thermal cracking of bionaphtha in the presence of steam, removing propene and at least some of the propane, gas phase oxidation to give acrylic acid and polymerization to give water-absorbing polymer particles.

Water-absorbing polymer particles are used to produce diapers, tampons, sanitary napkins and other hygiene articles, but also as water-retaining agents in market gardening. The water-absorbing polymer particles are also referred to as superabsorbents.

The production of water-absorbing polymer particles is described in the monograph "Modern Superabsorbent Polymer Technology", F. L. Buchholz and A. T. Graham, Wiley-VCH, 1998, pages 71 to 103.

The properties of the water-absorbing polymer particles can be adjusted, for example, via the amount of crosslinker used. With an increasing amount of crosslinker, the centrifuge retention capacity (CRC) falls and the absorption under a pressure of 21.0 g/cm$^2$ (AUL0.3 psi) passes through a maximum.

EP 2 395 029 A1 discloses the use of an acrylic acid comprising at least 0.04% by weight of propionic acid for production of water-absorbing polymer particles. The examples show that the properties of the water-absorbing polymer particles obtained, for example the centrifuge retention capacity (CRC), can be improved by the presence of propionic acid in the polymerization.

DE 103 36 786 A1 discloses a process for preparing acrylic acid by two-stage gas phase oxidation of propene and the subsequent workup of the reaction mixture.

EP 2 290 045 A1 discloses the preparation of propene from bionaphtha.

It was an object of the present invention to provide an improved process for producing water-absorbing polymer particles.

It was a further object of the present invention to provide an inexpensive process for producing water-absorbing polymer particles based on renewable raw materials.

The object was achieved by a process for producing water-absorbing polymer particles, comprising the steps of
i) thermally cracking bionaphtha based on natural oils and/or fats in the presence of steam to give a mixture comprising propane and propene,
ii) removing propene and at least some of the propane from the mixture obtained in step i),
iii) gas phase oxidation of the propene/propane mixture obtained in step ii) to give acrylic acid and
iv) polymerizing the acrylic acid obtained in step iii) to give water-absorbing polymer particles.

Bionaphtha in the context of this invention is all natural oils and/or fats, and derivatives thereof. For instance, it is possible to hydrolyze the natural oils and/or fats and to use only the fatty acids obtained as bionaphtha, as described in EP 2 290 034 A1. It is also possible to hydrogenate the fatty acids removed, as described in EP 2 290 045 A1. In a particularly preferred embodiment of the present invention, bionaphtha based on palm oil is used.

The gas phase oxidation of propene to acrylic acid is not subject to any restrictions and is preferably performed in two stages, i.e. in a first stage from propene to acrolein and in a second stage from acrolein to acrylic acid.

The present invention is based on the finding that more propane is formed relative to propene in the thermal cracking of bionaptha. Owing to the similar boiling point, the separation of propane from propene is inconvenient and costly.

If propene is then converted in a gas phase oxidation to acrylic acid, propane present in the propene is oxidized under these conditions to propionic acid. The separation of propionic acid from acrylic acid is likewise inconvenient and costly owing to similar boiling points.

For improvement of the product properties, the presence of propionic acid is in fact desirable in the production of water-absorbing polymer particles. The acrylic acid used comprises preferably from 0.02 to 2.0% by weight, more preferably from 0.03 to 1.0% by weight and most preferably from 0.04 to 0.5% by weight of propionic acid.

Therefore, in the case of use of acrylic acid based on bionaphtha, it is possible to dispense with a particularly complex purification of the propene or of the acrylic acid.

The propene used for gas phase oxidation comprises preferably from 3.4 to 30% by weight, more preferably from 3.8 to 15% by weight and most preferably from 4.2 to 7.5% by weight of propane, based in each case on propene.

It is also possible through simultaneous use of bionaphtha and naphtha to adjust the propionic acid content to the desired value, for example by combined use of bionaphtha and naphtha in the thermal cracking in step 1 (FIG. 1).

Figure 2:
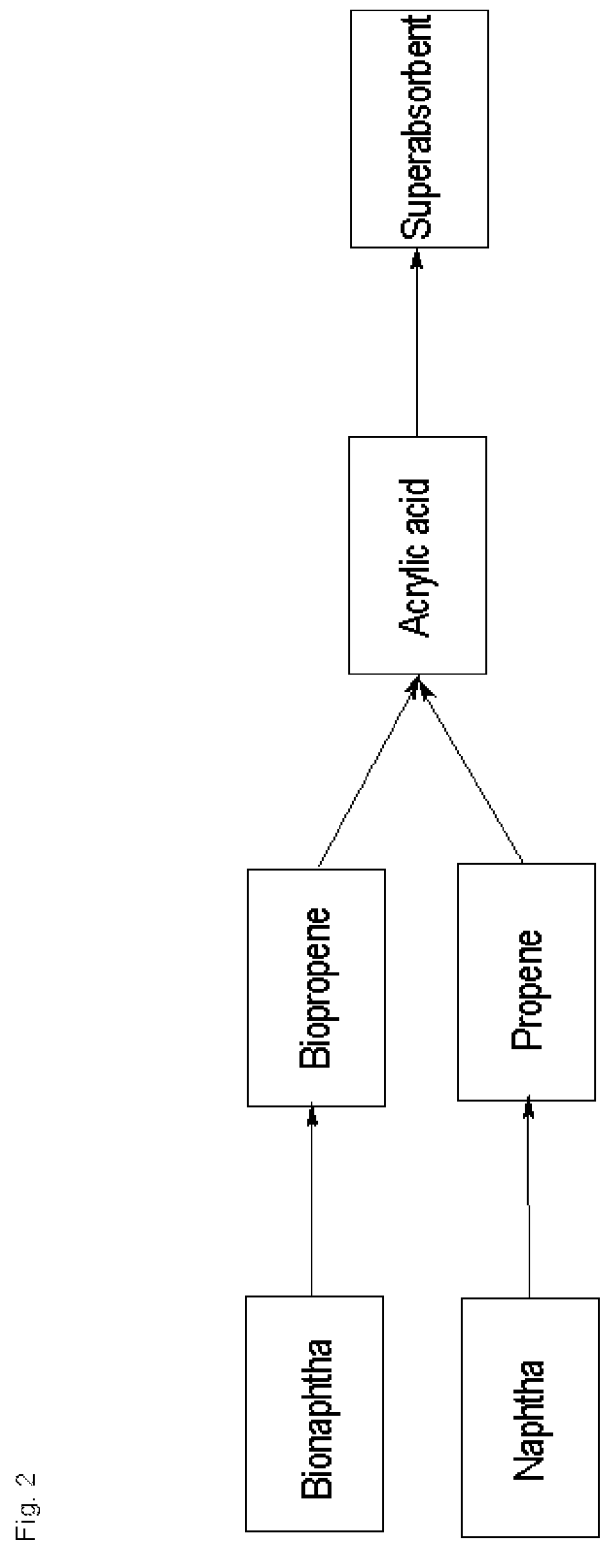

It is, however, also possible to convert bionaphtha and naphtha separately to propene and to convert the biopropene and propene thus obtained together to acrylic acid (FIG. 2).

Figure 3:
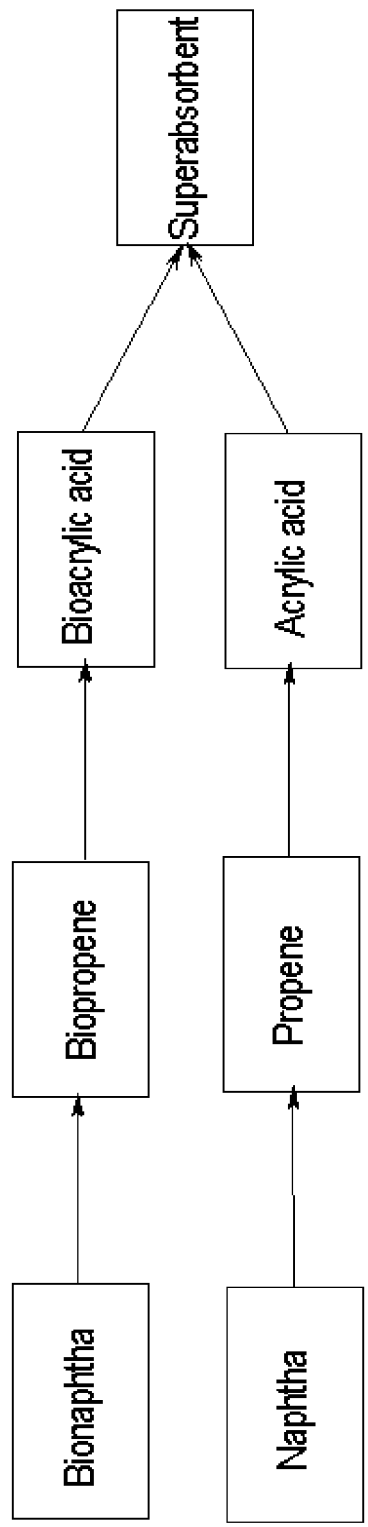

In addition, it is possible to convert bionaphtha and naphtha separately to propene, the biopropene and propene thus obtained separately to acrylic acid, and the bioacrylic acid and acrylic acid thus obtained together to water-absorbing polymer particles (FIG. 3).

In addition, it is possible to switch only a portion of the amount used in the thermal cracking of naphtha (steamcracking) to bionaphtha, for example to exactly the amount theoretically necessary through the propene and acrylic acid stages for production of the water-absorbing polymer particles. Thus, it is also possible to produce small amounts of water-absorbing polymer particles on the basis of renewable raw materials without losing the cost advantage of large production plants.

The water-absorbing polymer particles are produced, for example, by polymerizing a monomer solution or suspension comprising:
a) acrylic acid which may be at least partly neutralized,
b) at least one crosslinker,
c) at least one initiator,
d) optionally one or more ethylenically unsaturated monomers copolymerizable with the monomers mentioned under a) and
e) optionally one or more water-soluble polymers,
and are typically water-insoluble.

The proportion of acrylic acid and/or salts thereof in the total amount of monomers is preferably at least 50 mol %, more preferably at least 90 mol % and most preferably at least 95 mol %.

The acrylic acid used typically comprises polymerization inhibitors, preferably hydroquinone monoethers, as storage stabilizers.

The monomer solution therefore comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight of hydroquinone monoether, based in each case on the unneutralized acrylic acid. For example, the monomer solution can be prepared by using an acrylic acid with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the acrylic acid. In addition, polyvalent metal salts which can form coordinate bonds with at least two acid groups of the acrylic acid are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05 to 1.5% by weight, more preferably 0.1 to 1% by weight and most preferably 0.2 to 0.6% by weight, based in each case on acrylic acid. With rising crosslinker content, the centrifuge retention capacity (CRC) falls and the absorption under a pressure of 21.0 g/cm$^2$ passes through a maximum.

The initiators c) used may be all compounds which generate free radicals under the polymerization conditions, for example thermal initiators, redox initiators or photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with acrylic acid are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

Further suitable monomers d) are, for example, ethylenically unsaturated carboxylic acids, such as methacrylic acid and itaconic acid, and ethylenically unsaturated sulfonic acids such as styrenesulfonic acid and 2-acrylamido-2-methylpropanesulfonic acid (AMPS).

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight and most preferably from 50 to 65% by weight. It is also possible to use monomer suspensions, i.e. monomer solutions with excess acrylic acid, for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel which has to be comminuted in a further process step, for example in an extruder or kneader.

To improve the drying properties, the comminuted polymer gel obtained by means of a kneader can additionally be extruded.

The acid groups of the resulting polymer gels have typically been partially neutralized. Neutralization is preferably carried out at the monomer stage. This is typically accomplished by mixing in the neutralizing agent as an aqueous solution or preferably also as a solid. The degree of neutralization is preferably from 25 to 95 mol %, more preferably from 30 to 80 mol % and most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably 10 to 30 mol % and more preferably 15 to 25 mol % of the acid groups before the polymerization by adding a portion of the neutralizing agent directly to the monomer solution and setting the desired final degree of neutralization only after the polymerization, at the polymer gel stage. When the polymer gel is at least partly neutralized after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The polymer gel is then preferably dried with a belt drier until the residual moisture content is preferably 0.5 to 15% by weight, more preferably 1 to 10% by weight and most preferably 2 to 8% by weight, the residual moisture content being determined by EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the gel before the drying is preferably from 25 to 90% by weight, more preferably from 35 to 70% by weight and most preferably from 40 to 60% by weight. However, a fluidized bed drier or a paddle drier may optionally also be used for drying purposes.

Thereafter, the dried polymer gel is ground and classified, and the apparatus used for grinding may typically be single or multistage roll mills, preferably two or three-stage roll mills, pin mills, hammer mills or vibratory mills.

In a preferred embodiment of the present invention, an aqueous monomer solution is dropletized and the droplets obtained are polymerized in a heated carrier gas stream. It is possible here to combine the process steps of polymerization and drying, as described in WO 2008/040715 A2, WO 2008/052971 A1 and especially in WO 2011/026876 A1. In this preferred embodiment, the particle size is adjusted via the size of the droplets obtained.

The mean particle size of the water-absorbing polymer particles is preferably at least 200 µm, more preferably from 250 to 600 µm and very particularly from 300 to 500 µm. The mean particle size can be determined by means of EDANA recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of particles having a particle size of greater than 150 µm is preferably at least 90% by weight, more preferably at least 95% by weight and most preferably at least 98% by weight.

Polymer particles with too small a particle size lower the permeability (SFC). The proportion of excessively small polymer particles ("fines") should therefore be low.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

If a kneading reactor is used for polymerization, the excessively small polymer particles are preferably added during the last third of the polymerization.

If the excessively small polymer particles are added at a very early stage, for example actually to the monomer solution, this lowers the centrifuge retention capacity (CRC) of the resulting water-absorbing polymer particles. However, this can be compensated for, for example, by adjusting the amount of crosslinker b) used.

If the excessively small polymer particles are added at a very late stage, for example not until an apparatus connected downstream of the polymerization reactor, for example an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 µm is preferably at least 90% by weight, more preferably at least 95% by weight, most preferably at least 98% by weight.

The proportion of particles having a particle size of 150 to 850 µm is preferably at least 90% by weight, more preferably at least 95% by weight and most preferably at least 98% by weight.

Polymer particles with too great a particle size lower the free swell rate. The proportion of excessively large polymer particles should therefore likewise be small.

Excessively large polymer particles are therefore typically removed and recycled into the grinding of the dried polymer gel.

To further improve the properties, the polymer particles can be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amido acetals in DE 103 34 584 A1, oxetanes and cyclic ureas in EP 1 199 327 A2 and morpholine-2,3-dione and derivatives thereof in WO 2003/031482 A1.

Preferred surface postcrosslinkers are ethylene carbonate, ethylene glycol diglycidyl ether, reaction products of polyamides with epichlorohydrin and mixtures of propylene glycol and 1,4-butanediol.

Very particularly preferred surface postcrosslinkers are 2-hydroxyethyl-2-oxazolidinone, 2-oxazolidinone and 1,3-propanediol.

In addition, it is also possible to use surface postcrosslinkers which comprise additional polymerizable ethylenically unsaturated groups, as described in DE 37 13 601 A1.

The amount of surface postcrosslinker is preferably 0.001 to 2% by weight, more preferably 0.02 to 1% by weight and most preferably 0.05 to 0.2% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are hydroxide, chloride, bromide, sulfate, hydrogensulfate, carbonate, hydrogencarbonate, nitrate, phosphate, hydrogenphosphate, dihydrogenphosphate and carboxylate, such as acetate, citrate and lactate. Salts with different counterions are also possible, for example basic aluminum salts such as aluminum monoacetate or aluminum monolactate. Aluminum sulfate, aluminum monoacetate and aluminum lactate are preferred. Apart from metal salts, it is also possible to use polyamines as polyvalent cations.

The amount of polyvalent cation used is, for example, 0.001 to 1.5% by weight, preferably 0.005 to 1% by weight and more preferably 0.02 to 0.8% by weight, based in each case on the polymer particles.

The surface postcrosslinking is typically performed in such a way that a solution of the surface postcrosslinker is sprayed onto the dried polymer particles. After the spray application, the polymer particles coated with surface postcrosslinker are dried thermally, and the surface postcrosslinking reaction can take place either before or during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting characteristics and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The thermal drying is preferably carried out in contact driers, more preferably paddle driers, most preferably disk driers. Suitable driers are, for example, Hosokawa Bepex® Horizontal Paddle Dryers (Hosokawa Micron GmbH; Leingarten; Germany), Hosokawa Bepex® Disc Dryers (Hosokawa Micron GmbH; Leingarten; Germany), Holo-Flite® driers (Metso Minerals Industries Inc.; Danville; USA) and Nara Paddle Dryers (NARA Machinery Europe; Frechen; Germany). Moreover, fluidized bed driers may also be used.

The drying can be effected in the mixer itself, by heating the jacket or blowing in warm air. Equally suitable is a downstream drier, for example a shelf drier, a rotary tube oven or a heatable screw. It is particularly advantageous to effect mixing and drying in a fluidized bed drier.

Preferred drying temperatures are in the range of 100 to 250° C., preferably 120 to 220° C., more preferably 130 to 210° C. and most preferably 150 to 200° C. The preferred residence time at this temperature in the reaction mixer or drier is preferably at least 10 minutes, more preferably at least 20 minutes, most preferably at least 30 minutes, and typically at most 60 minutes.

In a preferred embodiment of the present invention, the water-absorbing polymer particles are cooled after the thermal drying. The cooling is preferably performed in contact coolers, more preferably paddle coolers and most preferably disk coolers. Suitable coolers are, for example, Hosokawa Bepex® Horizontal Paddle Coolers (Hosokawa Micron GmbH; Leingarten; Germany), Hosokawa Bepex® Disc Coolers (Hosokawa Micron GmbH; Leingarten; Germany), Holo-Flite® coolers (Metso Minerals Industries Inc.; Danville; USA) and Nara Paddle Coolers (NARA Machinery Europe; Frechen; Germany). Moreover, fluidized bed coolers may also be used.

In the cooler, the water-absorbing polymer particles are cooled to 20 to 150° C., preferably 30 to 120° C., more preferably 40 to 100° C. and most preferably 50 to 80° C.

Subsequently, the surface postcrosslinked polymer particles can be classified again, excessively small and/or excessively large polymer particles being removed and recycled into the process.

To further improve the properties, the surface postcrosslinked polymer particles can be coated or remoisturized.

The remoisturizing is preferably performed at 30 to 80° C., more preferably at 35 to 70° C., most preferably at 40 to 60° C. At excessively low temperatures, the water-absorbing polymer particles tend to form lumps, and, at higher temperatures, water already evaporates to a noticeable degree. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging. The remoisturizing is advantageously performed in the cooler after the thermal drying.

Suitable coatings for improving the free swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

The water-absorbing polymer particles have a centrifuge retention capacity (CRC) of typically at least 15 g/g, preferably at least 20 g/g, more preferably at least 22 g/g, especially preferably at least 24 g/g and most preferably at least 26 g/g. The centrifuge retention capacity (CRC) of the water-absorbing polymer particles is typically less than 60 g/g. The centrifuge retention capacity (CRC) is determined by EDANA recommended test method No. WSP 241.2-05 "Fluid Retention Capacity in Saline, After Centrifugation".

The invention claimed is:

1. A process for producing water-absorbing polymer particles, comprising
    i) thermally cracking a naphtha and a bionaphtha from a natural oil and/or fat in the presence of steam to give a mixture comprising propane and propane,
    ii) removing propene and at least some of the propane from the mixture obtained in step i),
    iii) gas phase oxidation of the propene/propane mixture obtained in step ii) to give acrylic add comprising from 0.02 to 2.0% by weight of propionic acid, and
    iv) polymerizing the acrylic add obtained in step iii) and from 0.05 to 1.5% by weight of a crosslinker based on acrylic add to give water-absorbing polymer particles, wherein the acrylic add used in step iv) comprises from 0.02 to 2.0% by weight of propionic add.

2. The process according to claim 1, wherein the natural oil is palm oil.

3. The process according to claim 1, wherein the gas phase oxidation in step iii) is performed in two stages.

4. The process according to claim 1, wherein the acrylic acid used in step iv) comprises 0.03 to 2.0% by weight of propionic acid.

5. The process according to claim 1, wherein the amount of crosslinker in step iv) is from 0.2 to 0.6% by weight, based on acrylic acid.

6. The process according to claim 1, wherein the water-absorbing polymer particles are surface postcrosslinked.

7. The process according to claim 1 wherein the water-absorbing polymer particles are coated with an inorganic inert substance.

* * * * *

UNITED STATES PATENT AND TRADEMARK OFFICE
CERTIFICATE OF CORRECTION

PATENT NO. : 9,822,197 B2  
APPLICATION NO. : 14/441203  
DATED : November 21, 2017  
INVENTOR(S) : Klaus Dieter Hörner et al.

Page 1 of 1

It is certified that error appears in the above-identified patent and that said Letters Patent is hereby corrected as shown below:

In the Claims

At Column 9, Line 24, Claim 1 "propane," should be -- propene, --.

At Column 10, Line 2, Claim 1 "acrylic add" should be -- acrylic acid --.

At Column 10, Line 4, Claim 1 "acrylic add" should be -- acrylic acid --.

At Column 10, Line 6, Claim 1 "acrylic add" should be -- acrylic acid --.

At Column 10, Line 7, Claim 1 "acrylic add" should be -- acrylic acid --.

At Column 10, Line 8, Claim 1 "propionic add." should be -- propionic acid. --.

At Column 10, Line 22, Claim 7 "claim 1" should be -- claim 1, --.

Signed and Sealed this  
First Day of May, 2018

Andrei Iancu  
*Director of the United States Patent and Trademark Office*